(12) United States Patent
Steffens et al.

(10) Patent No.: US 7,575,660 B2
(45) Date of Patent: Aug. 18, 2009

(54) PROCESS FOR THE DISTILLATIVE SEPARATION OF AQUEOUS AMINE SOLUTIONS

(75) Inventors: Friedhelm Steffens, Leverkusen (DE); Rainer Buse, Köln (DE); Bill Brady, Düsseldorf (DE)

(73) Assignee: Bayer MaterialScience AG, Leverkusen (DE)

( * ) Notice: Subject to any disclaimer, the term of this patent is extended or adjusted under 35 U.S.C. 154(b) by 690 days.

(21) Appl. No.: 11/138,991

(22) Filed: May 26, 2005

(65) Prior Publication Data

US 2005/0263385 A1 Dec. 1, 2005

(30) Foreign Application Priority Data

Jun. 1, 2004 (DE) ....................... 10 2004 026 626

(51) Int. Cl.
*B01D 3/00* (2006.01)
*C07C 51/44* (2006.01)
*C07C 209/84* (2006.01)
*C07C 209/86* (2006.01)

(52) U.S. Cl. ............................. 203/14; 203/25; 203/78; 203/80; 203/99; 203/DIG. 19; 564/437

(58) Field of Classification Search .................... 203/14, 203/25, 27, 78, 80, 99, DIG. 19; 564/305, 564/437

See application file for complete search history.

(56) References Cited

U.S. PATENT DOCUMENTS

| 3,356,728 | A | 12/1967 | Cimerol et al. | ............. 661/580 |
|---|---|---|---|---|
| 3,356,729 | A | 12/1967 | Denton et al. | ............. 661/580 |
| 3,431,085 | A | 3/1969 | Cimerol et al. | ............. 661/288 |
| 3,546,296 | A | 12/1970 | Gobron et al. | ................ 15/580 |
| 3,761,521 | A | 9/1973 | Alheritiere et al. | ........... 19/580 |
| 3,781,373 | A | 12/1973 | Gobron et al. | ............ 15/635 C |
| 3,849,261 | A * | 11/1974 | Gau | ............................ 203/39 |
| 3,882,048 | A | 5/1975 | Thelen et al. | ................. 22/464 |
| 3,895,065 | A | 7/1975 | Alheritiere et al. | ........ 19/583 R |
| 4,720,326 | A | 1/1988 | Beckhaus et al. | ............. 236/14 |
| 5,728,880 | A | 3/1998 | Beckhaus et al. | ........... 794/305 |
| 6,635,151 | B1 * | 10/2003 | Bocquenet et al. | ........... 203/14 |
| 6,821,396 | B2 | 11/2004 | Wolfert et al. | ..................... 1/43 |
| 6,913,674 | B2 | 7/2005 | Wölfert et al. | .................... 1/43 |
| 2005/0000790 | A1 | 1/2005 | Beck et al. | ......................... 3/2 |

FOREIGN PATENT DOCUMENTS

| DE | 2 106 664 | 8/1972 |
|---|---|---|
| DE | 21 35 154 | 4/1980 |
| GB | 768111 | 2/1957 |
| GB | 1017646 | 1/1966 |
| GB | 1 490 313 | 11/1977 |

* cited by examiner

*Primary Examiner*—Virginia Manoharan
(74) *Attorney, Agent, or Firm*—John E. Mrozinski, Jr.; Noland J. Cheung

(57) ABSTRACT

The invention relates to an energy efficient process for the distillative working-up of aqueous amine solutions that occur in the catalytic hydrogenation of nitroaromatic compounds. In this process, the amine is freed from water and also the water is obtained free from amine and low-boiling compounds and the concentrated low-boiling compounds are obtained.

9 Claims, 1 Drawing Sheet

PROCESS FOR THE DISTILLATIVE SEPARATION OF AQUEOUS AMINE SOLUTIONS

FIELD OF THE INVENTION

The present invention relates to an energy-efficient process for the distillative working-up of aqueous amine solutions that are obtained in the catalytic hydrogenation of nitroaromatic compounds. In this process, the amine can be freed from water; water can be obtained that is free of amine and low-boiling compounds; and concentrated low-boiling compounds can be removed.

BACKGROUND OF THE INVENTION

It is known (DE-A-1 542 544, DE-A-1 947 851, DE-A-2 106 644, DE-A-2 135 154, DE-A-2 214 056, DE-A-2 456 308, BE-PS-631 964, BE-PS-661 047, BE-PS-661 946, FR-PS 1 359 438 or GB-PS 768 111) that aromatic diamines can be prepared by catalytic hydrogenation of the corresponding aromatic dinitro compounds. The hydrogenation may take place under the combined use of solvents such as for example low-boiling alcohols such as methanol, ethanol or isopropanol, but may also be carried out without the use of such foreign solvents. The hydrogenation may be carried out with the aid of catalysts dispersed in the reaction mixture, which are then separated by sedimentation or filtration and optionally recycled to the process.

Up to now, the working-up of the reaction mixture was carried out in such a way that a mixture of aromatic diamines and water of reaction present after separation of the optionally co-used auxiliary solvent was first of all continuously freed from water under normal pressure in a distillation column and the diamine occurring as distillation residue was then optionally freed in further process steps from still adhering water and from organic impurities that were possibly still present. With this procedure mixtures of water with steam-volatile organic byproducts, such as occur in the hydrogenation of the dinitroaromatic compounds, are always formed as distillates. These byproducts are for example aromatic or cycloaliphatic monoamines and/or cycloaliphatic alcohols, i.e. for example in the case of the production of diaminotoluene, are toluidines, perhydrotoluidines and/or methylcyclohexanols.

These steam-volatile byproducts cause the overhead distilled water to be highly contaminated with these compounds. In EP 0236 839 B1, a process for the distillative working-up of such aqueous amine solutions is described, in which a waste water that is far less contaminated with organic impurities is obtained. To this end, the mixture is separated in a distillation column with side extraction. The vapors of the distillation column are condensed, and the liquid phase that is thereby formed is passed through a phase separation apparatus, in which steam-volatile organic byproducts are removed as organic phase from the vapor condensate. The aqueous phase is returned to the head of the distillation column. The water that is largely freed from steam-volatile organic impurities is removed via a side stream. The diamines freed from water and steam-volatile impurities are formed in this case as bottom product. A common feature of all these processes is, however, high energy consumption: 1.2 to 2 kg of heating steam have to be used per kg of water to be separated.

SUMMARY OF THE INVENTION

The present invention therefore, provides a simple and economical process for the distillative separation of the aqueous amine solutions that occur in the catalytic hydrogenation of the corresponding nitroaromatic compounds. The inventive process can be operated with low energy consumption and the separated water can be obtained substantially free from steam-volatile organic impurities.

These and other advantages and benefits of the present invention will be apparent from the Detailed Description of the Invention herein below.

BRIEF DESCRIPTION OF THE FIGURES

The present invention will now be described for purposes of illustration and not limitation in conjunction with the figures, wherein.

DETAILED DESCRIPTION OF THE INVENTION

Figure 1:
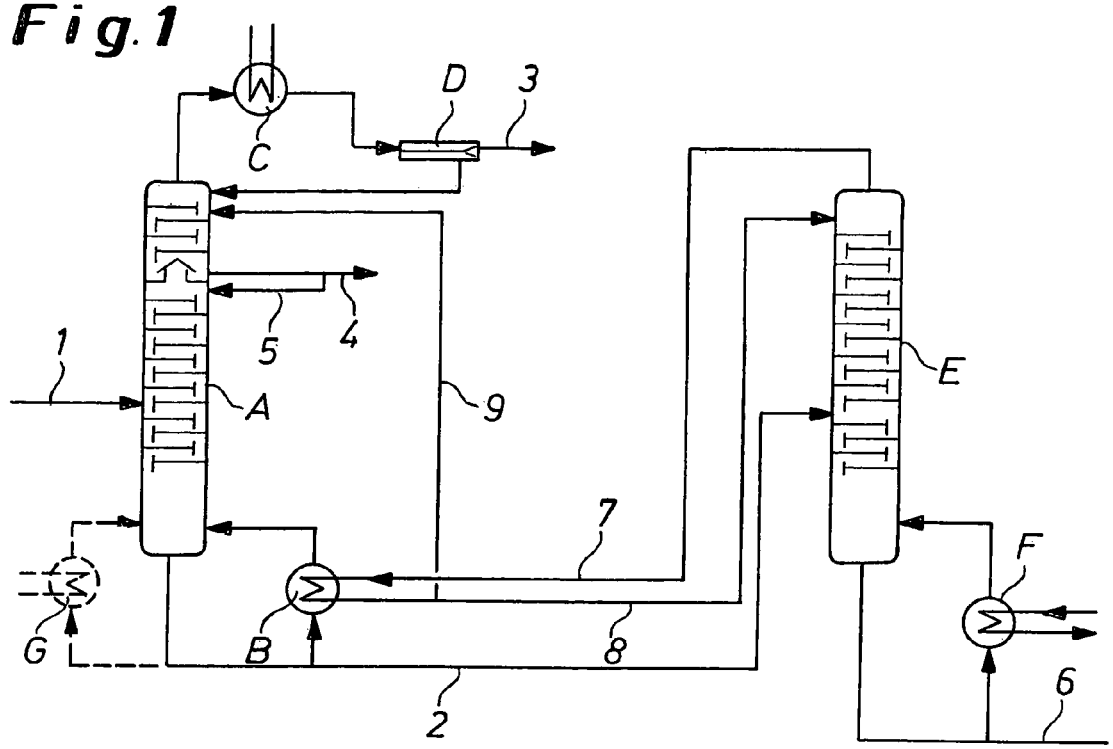
FIG. 1 shows a diagrammatic representation of one embodiment of the inventive process, in which the first distillation column is operated at the lower absolute pressure of 0.1 to 10 bar.

The present invention will now be described for purposes of illustration and not limitation. Except in the operating examples, or where otherwise indicated, all numbers expressing quantities percentages and so forth in the specification are to be understood as being modified in all instances by the term "about."

The present invention relates to a process for the distillative separation of aqueous amine solutions that occur in the hydrogenation of nitroaromatic compounds, which process is characterized in that a) the distillation is carried out in at least two distillation columns connected in series and operated at different pressures, in which at least one distillation column is operated at higher absolute pressures at the column head of 2 to 20 bar and at least one distillation column is operated at lower absolute pressures at the column head of 0.1 to 10 bar, b) the vapors leaving the distillation column operating at higher pressures are at least partially condensed and the heat that is thereby released is used to heat the bottom of the distillation column operating at the lower pressures, c) the amine solution is fed into the first of the at least two distillation columns connected in series, and the bottom product of the first distillation column is at least partially removed and fed into the second distillation column, and d) the purified amine is removed as bottom product from the last distillation column.

The present invention also relates to a process for the distillative separation of aqueous amine solutions that occur in the hydrogenation of nitroaromatic compounds, the process being characterized in that a) the distillation is carried out in at least two distillation columns connected in series and operated at different pressures, in which at least one distillation column is operated at higher absolute pressures at the column head of 2 to 20 bar and at least one distillation column is operated at lower absolute pressures at the column head of 0.1 to 10 bar, b) the vapors leaving the distillation column operating at higher pressures are at least partially condensed and the heat that is thereby released is used to heat the bottom of the distillation column operating at the lower pressures, c) the amine solution is fed into the first of the at least two distillation columns connected in series, and the bottom product of the first distillation column is at least partially removed and fed into the second distillation column, d) the purified amine is removed as bottom product from the last distillation column, e) the vapors from the distillation column operating at the lower pressures are condensed, the steam-volatile low-boiling compounds are separated therefrom by phase separation, and the remaining aqueous condensed vapors are recycled as reflux stream to the distillation column operating at the lower pressures, f) the vapor condensate from the distillation column operating at the higher pressures is fed in part to the head of the distillation column operating at the lower pressures and in part as reflux stream to the head of the column operating at the higher pressures, and g) water is removed as side stream from the distillation column operating at the lower pressures.

Preferably, the distillation is carried out in two distillation columns connected in series. It is, however, also possible to use more than two distillation columns that are operated as a cascade with falling or rising pressures, in which the vapors from the column operating at the next higher pressure may be used to heat the bottom of the adjacent column operating at the next lower pressure. The separation of the low-boiling compounds and water preferably takes place in the column that is operated at the lowest pressure, because the density difference is then a maximum. It is, however, also possible to carry out the separation of the low-boiling compounds and water in the column at the higher pressure or alternatively in both distillation columns. The purified amine is then removed in step d) in the last distillation column, and in the case of a total of two distillation columns connected in series, accordingly in the second distillation column.

By means of the process according to the invention the aqueous amine solutions containing byproducts can be separated under minimum expenditure of energy specifically into the three constituents: amine, by-product and pure water. The specific feature of the inventive process is that this substance separation is carried out in at least two separate columns at different pressures, in which one column heats the other column. The energy consumption of the entire process is thus significantly reduced. The steam-volatile byproducts may be condensed at the head of one of the columns, removed and condensed as vapors, and separated from organic constituents by means of a liquid-liquid phase separation apparatus and then discharged.

Preferably the process according to the invention is used for the production of aromatic diamines, in particular, toluenediamine.

Starting materials for the process according to the invention are preferably aqueous amine solutions such as occur in the hydrogenation of dinitroaromatic compounds. More preferably used in the process according to the present invention are aqueous amine solutions such as occur in the hydrogenation of industrial dinitrotoluenes, and which have previously been freed by distillation from the auxiliary solvent optionally co-used in the hydrogenation, such as the simple alcohols mentioned above. These solutions are preferably from 50-70 wt. %, more preferably from 55-65 wt. % solutions (referred to the weight of the solution) of diaminotoluenes in water, these solutions preferably containing up to 5 wt. % (referred to the weight of the solution), more preferably from 500-5000 ppm (by weight) of steam-volatile impurities of the type mentioned hereinbefore by way of example. These diamines include for example pure 2,4-diaminotoluene or its industrial mixtures with up to 40 wt. %, referred to the total weight, of 2,6-diaminotoluene and optionally up to 5 wt. %, referred to the total mixture, of other isomeric diaminotoluenes, the percentages totaling in each case 100%.

To carry out the process according to the invention, there are preferably used two distillation columns, for example bubble plate, packing or packed columns, connected in series to one another. Preferably the two columns have from 12 to 50, more preferably from 20 to 40, theoretical separating plates (stages). The column under the lower pressure is preferably operated at a bottom temperature of from 60° to 150° C., more preferably from 90° to 110° C. The absolute pressure at the head of the column is preferably from 0.1 to 10 bar, more preferably from 0.5 to 6 bar.

The column under the higher pressure is preferably operated at a bottom temperature of from 120° to 240° C., more preferably from 180° to 220° C. The absolute pressure at the head of the column is from 2 to 20 bar, more preferably from 3 to 6 bar. The pressures in the two columns are preferably chosen so that in the heat exchanger, in which the vapors from the column under the higher pressure are condensed and at the same time the bottom of the column under the lower pressure is heated, there is at least a temperature difference between the condensing and evaporating side of preferably at least 10° C., more preferably at least 20° C. The operating conditions to be adjusted in the two columns obviously depend on the nature of the mixtures to be worked up, the temperature of the heating steam, and the desired vapor temperature of the low pressure column. By suitably choosing the operating conditions these vapors may for example be used to evaporate solvents, to heat product streams or to generate process steam. Depending on the heating steam temperature, the external heating may take place in one apparatus or in several apparatuses.

Two different embodiments of the process according to the invention are described herein for the separation of aqueous amine solutions that occur in the hydrogenation of industrial dinitrotoluenes and that have been freed beforehand by distillation from auxiliary solvent optionally co-used in the hydrogenation, such as alcohols. These embodiments are however not restricted to the separation of these special aqueous amine solutions.

In a first embodiment of the process according to the present invention, the first of the at least two distillation columns connected in series is operated at a lower absolute pressure in the range from 0.1 to 10 bar. The second distillation column, (or in the case of a total of more than two distillation columns, one of the subsequent distillation columns), is thus operated at higher pressures than the first distillation column. The aqueous amine solution to be separated is fed into the first column from above the bottom evaporator, preferably between the second and the eighth theoretical plate (from the bottom of the column). The bottom of the first column is thus heated by the condensation of the vapors from the second column. The heat exchange may in this case take place by means of internal evaporators (e.g. heating bundles) or external evaporators (e.g. circulation evaporators). In parallel to this, a further evaporator may also be used, for example, to utilize a further energy source at a lower temperature.

The vapors of the first column are condensed and, after separation of the steam-volatile organic phase (of the steam-volatile low boiling byproducts) by phase separation, are recycled to the head of the first column. The distillate removal, i.e. the removal of the water, is effected by means of a removal floor via a side stream that is arranged at least 4, more preferably from 5 to 15 theoretical plates below the head of the first column and at least 8, more preferably from 12 to 25 theoretical plates above the bottom of the first column. In this connection the volume ratio of reflux stream (below the removal site) to the removal of the water is preferably at least 0.2, more preferably from 0.3 to 0.6.

The bottom product of the first column is fed into the second column above the bottom evaporator, preferably between the second and the eighth theoretical plate (from the bottom of the column). The bottom of the second column is heated by external heating agents, for example by means of heating steam. The heating may be effected by means of internal evaporators (e.g. heating bundles) or external evaporators (e.g. circulation evaporators). The heating may be carried out by means of an individual evaporator or by several evaporators at different heating temperatures connected in series (e.g. preferably steam, but also internal process substance streams).

The vapors from the second column, which is operated at a higher absolute pressure of from 2 to 20 bar, are used to heat the first column. The vapor condensate from the second column is fed in part as reflux stream to the head of the second column and in part to the head of the first column for the removal of the steam-volatile secondary components. The water largely freed from secondary components is then removed as side stream from the first column.

The volume ratio of the proportion of the vapor condensate that is fed as reflux stream to the second column to the proportion of the vapor condensate that is fed to the head of the first column is preferably at least 0.2 and more preferably from 0.3 to 0.6. The rectifying section of the second column preferably has at least 15 theoretical plates.

In another embodiment of the process according to the present invention, the first column of the two distillation columns connected in series is operated under a higher absolute pressure of 2 to 20 bar. The second distillation column (or in the case of a total of more than two distillation columns, one of the subsequent distillation columns) is thus operated at lower pressures than the first distillation column. The aqueous amine solution to be separated is fed into the first column above the bottom evaporator, preferably between the second and eighth theoretical plate (from the bottom of the column). The bottom of this column is heated with external heating agents, e.g. by means of heating steam. The heating may be carried out by means of internal evaporators (e.g. heating bundles) or external evaporators (e.g. circulation evaporators). In parallel to this, a further evaporator may also be employed, for example to utilize a further energy source.

The vapors from the first column are used, after condensation and heat exchange, to heat the second column. The heat exchange may in this connection be effected by means of internal evaporators (e.g. heating bundles) or external evaporators (e.g. circulation evaporators). After condensation of the vapors from the first column, a part of the vapors is fed as reflux stream to the head of the first column, and a part is fed to the head of the second column in order to remove the steam-volatile secondary components (reflux ratio preferably at least 0.1, more preferably from 0.15 to 0.6). The rectifying section of the first column has in this connection at least 15 theoretical separating plates.

The bottom product of the first column is fed into the second column above the bottom evaporator, preferably between the second and the eighth theoretical plate (from the bottom of the column). The bottom of the second column is thus heated by condensation of the vapors from the first column and by heat exchange. The heating may be effected by means of internal evaporators (e.g. heating bundles) or external evaporators (e.g. circulation evaporators). To achieve a complete removal of water or to adjust the desired final concentration of water, the second column is operated with an additional evaporator, which may be operated with heating steam. Depending on the temperature of the heating steam and pressure level of the heating steam that is used, a plurality of evaporators connected in series and at different heating temperatures may also be used for this purpose (e.g. also internal process substance streams).

The vapors from the second column are condensed and, after separation of the steam volatile organic phase (the steam-volatile low-boiling point byproducts) by phase separation, are recycled to the head of the second column. The steam-volatile low-boiling compounds are removed in the upper part of the second column and the water largely freed from secondary components is removed as side stream. The distillate removal, i.e. the removal of the water, is effected by means of a removal floor above a side stream that is arranged at least 4, more preferably from 5 to 15 theoretical plates below the head of the second column and at least 8, more preferably 12 to 25 theoretical plates above the bottom of the second column. In this connection, the volume ratio of reflux stream (below the removal site) to the removal of the water is at least 0.2, more preferably from 0.3 to 0.6.

FIG. 1 shows a diagrammatic representation of a first embodiment of the process, in which first distillation column A is operated at an absolute pressure in the range from 0.1 to 10 bar and second distillation column E is operated at the higher absolute pressure in the range from 2 to 20 bar. The aqueous amine solution (stream 1) is fed into first column A and separated. The vapors are condensed in condenser C, and the low-boiling compounds are then separated in liquid-liquid separation apparatus D from the aqueous phase and removed as stream 3. The aqueous phase is recycled as reflux stream to the head of column A. The water from which organic constituents have been removed is separated in the side stream and in part is removed as stream 4 and in part is recycled as reflux stream 5. The bottom of column A is heated by evaporator B and optional additional heat exchanger or evaporator G.

The bottom product of first column A is in part removed and fed as stream 2 into second distillation column E.

The heating of evaporator B is effected by the vapors leaving second column E (stream 7). The vapors are in this connection condensed in evaporator B. The condensed vapors are then in part recycled as reflux stream to the head of second column E (stream 8) and in part fed to the head of first column A (stream 9), to remove the steam-volatile secondary components (reflux ratio preferably at least 0.1, more preferably 0.15 to 0.6).

The heating of second column E is effected by input of external energy, for example heating steam, into evaporator F. The purified amine is removed as stream 6 from the bottom of second column E.

Figure 2:
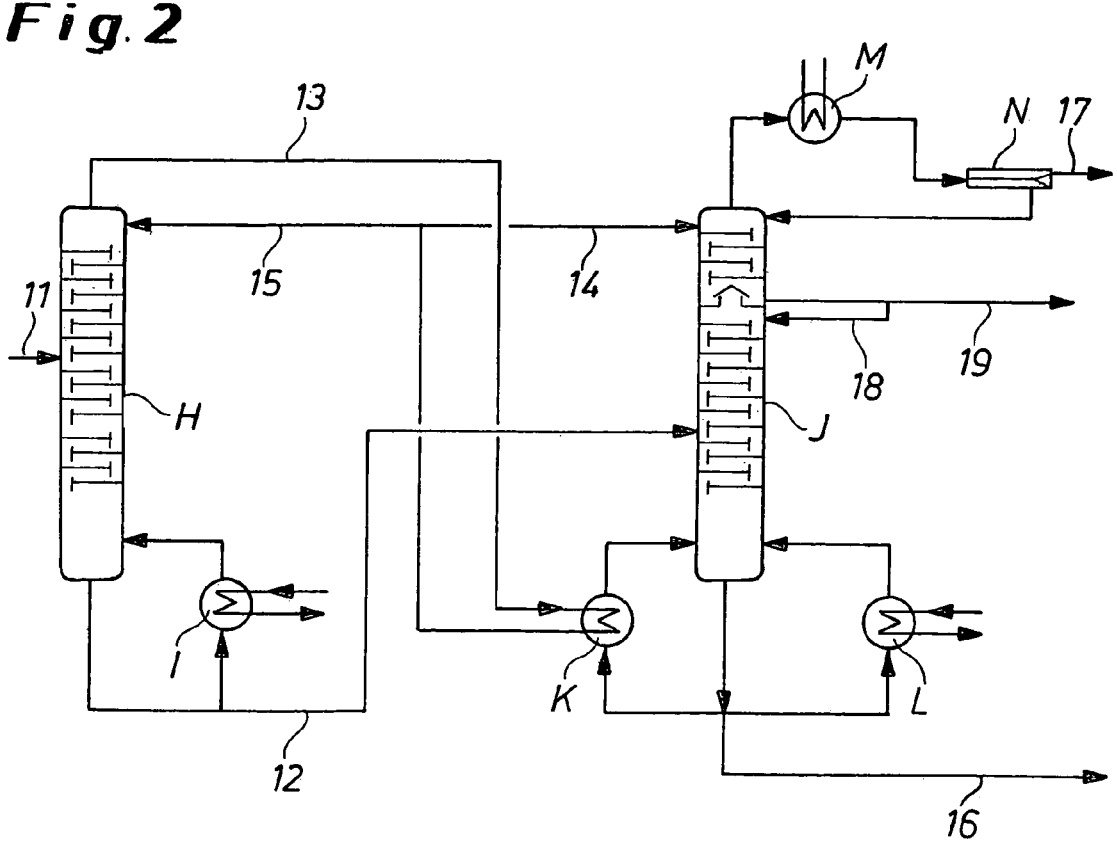
FIG. 2 illustrates a diagrammatic representation of a second embodiment of the process, in which the first distillation column is operated at the higher absolute pressure of 2 to 20 bar.

FIG. 2 shows a diagrammatic representation of a second embodiment of the process of the present invention, in which first distillation column H is operated at the higher absolute pressure of 2 to 20 bar and second distillation column J is operated at the lower absolute pressure in the range from 0.1 to 10 bar. The aqueous amine solution (stream 11) is fed into first column H and separated. The heating of the bottom of first column H is effected in this connection by input of external energy, for example heating steam, into evaporator I.

The bottom product of first column H is in part removed and fed as stream 12 into second distillation column J. The vapors leaving second column J are condensed in condenser M, and the low-boiling compounds from the aqueous phase are then separated in liquid-liquid separating apparatus N and removed as stream 17. The aqueous phase is recycled as reflux stream to the head of second column J. The water from which organic constituents have largely been removed is separated in the side stream and is removed in part as stream 19 and recycled in part as reflux stream 18. The bottom of column J is heated by evaporator L and evaporator K.

The heating of second column J by additional evaporator L is effected by input of external energy, for example heating steam. The heating of second column J by evaporator K is effected by the vapors leaving first column H as stream 13. The vapors are in this connection condensed in evaporator K. The condensed vapors are then recycled in part as reflux stream 14 (reflux ratio preferably at least 0.1, particularly preferably 0.15 to 0.6) to the head of second column J, in order to remove the steam-volatile secondary components, and are fed in part as stream 15 to the head of first column H.

The purified amine is removed as stream 16 from the bottom of second column J.

EXAMPLES

Example 1

According to the Embodiment Depicted in FIG. 1

In a first column A containing 36 stages, a solvent-free reaction mixture from the DNT hydrogenation was added to the fifth stage (plate) above the bottom of the column. The mixture was an approximately 57 wt. % solution of a diamine mixture containing 77.2 wt. % of 2,4-diaminotoluene, 19.3 wt. % of 2,6-diaminotoluene and 3.5 wt. % of other diaminotoluene isomers. The solution had a content of steam-volatile organic byproducts of 0.3 wt. %. The water content of the solution was correspondingly approximately 42.7 wt. %.

This first column A was operated at an absolute head pressure of 0.6 bar. A water content of 30 wt. % at approximately 93° C. was established in the bottom of the column A. The heating was effected with the vapors from the second column E. The column E was operated at 3 bar absolute pressure, and the vapors correspondingly had a temperature of 134° C. At the head of the first column A the low-boiling compounds were almost quantitatively separated as stream 3 from the feed, and the condensed water was recycled to the uppermost stage. The water was removed as side stream 10 stages below the head of the column, and in part was discharged as stream 4 and in part was recycled as reflux stream 5. To achieve a residual content of approximately 100 ppm in the distilled water, the side stream removal was operated at a reflux ratio of 0.3.

The bottom product of the first column (stream 2) was fed into the second column E, 5 stages above the bottom. This column had a total of 25 stages. A residual water content of 3 wt. % at approximately 180° C. was achieved in the bottom of the column E. The head product of the column E (vapor stream 7) was condensed in the evaporator B of the first column A. Three parts of the vapor condensate were recycled as reflux stream 8 to the second column E, and ten parts of the vapor condensate were fed as stream 9 to the uppermost stage of the first column A.

Example 2

According to the Embodiment of FIG. 2

In a first column H with 25 theoretical plates the reaction mixture from the DNT hydrogenation already described in Example 1 was fed to the fifth stage above the bottom of the column.

The column H was operated at an absolute head pressure of 3 bar; a water content of 30 wt. % at approximately 140° C. was established in the bottom of the column H. The heating of the bottom product in the evaporator I was effected by steam at a temperature of 160° C. The vapor stream 13 from the first column H was condensed in the evaporator K, in which at the same time the bottom product of the second column J was heated and evaporated. Three parts of the vapor condensate were recycled as reflux stream (stream 15) to the head of the first column H, and ten parts of the vapor condensate were fed as stream 14 to the head of the second column J.

The bottom product of the first column H (stream 12) was fed into the second column J, 5 stages above the bottom of the column. The column J had a total of 36 stages and was operated at an absolute head pressure of 3 bar. A residual water content of 3 wt. % at approximately 120° C. was achieved in the bottom of the column J. The vapors were condensed in the condenser M at the head of the second column J and the low-boiling compounds were separated almost quantitatively in the liquid-liquid separating apparatus N and discharged as stream 17. The condensed water was recycled to the uppermost stage. The water was removed as side stream 10 stages below the head, and in part was removed as stream 19 and in part recycled as reflux stream 18. To achieve a residual content of approximately 100 ppm in the distilled water, the side stream removal was operated at a reflux ratio of 0.3.

Compared to one-stage evaporation plants known in the art (e.g. EP 0 236 839 B1), 30 to 50% of the energy consumption can be saved with the present arrangement.

Although the invention has been described in detail in the foregoing for the purpose of illustration, it is to be understood that such detail is solely for that purpose and that variations can be made therein by those skilled in the art without departing from the spirit and scope of the invention except as it may be limited by the claims.

What is claimed is:

1. A process for the distillative separation of aqueous amine solutions from the hydrogenation of nitroaromatic compounds, comprising:
   a) carrying out distillation in at least two distillation columns connected in series and operated at different pressures, in which at least one of the distillation columns is operated at higher absolute pressures at the column head of about 2 to about 20 bar and at least one of the distillation columns is operated at lower absolute pressures at the column head of about 0.1 to about 10 bar;
   b) at least partially condensing vapors leaving the distillation column or columns operating at higher pressure and heating the bottom of the distillation column or columns operating at lower pressure with the heat released therefrom;
   c) feeding the amine solution into a first of the at least two distillation columns connected in series, and at least partially removing bottom product from the first distillation column and feeding the bottom product into the second distillation column, and
   d) removing purified amine as bottom product from a last distillation column connected in series.

2. The process according to claim 1, further comprising:
   e) condensing the vapors from the distillation column operating at the lower pressure, separating by phase separation steam-volatile low-boiling compounds therefrom, and recycling remaining aqueous condensed vapors as reflux stream to the distillation column operating at the lower pressure;

f) feeding condensate of the vapors from the distillation column operating at the higher pressure in part to a head of the distillation column operating at the lower pressure and in part as ref lux stream to a head of the column operating at the higher pressure; and g) removing water as side stream from the distillation column operating at the lower pressure.

3. The process according to claim 2, wherein the removal of the water in the side stream in step g) from the distillation column operating at lower pressure takes place at least four theoretical plates below the head of the column and at least eight theoretical plates above the bottom of the column.

4. The process according to claim 2, wherein the ratio of reflux to removal at the removal site for water in step g) is at least about 0.2.

5. The process according to claim 1, wherein the aqueous amine solutions comprise aromatic diamines.

6. The process according to claim 1, wherein the aqueous amine solutions comprise diaminetoluenes.

7. The process according to claim 1, wherein the first distillation column is operated at absolute pressures in the range from about 0.1 to about 10 bar.

8. The process according to claim 1, wherein the first distillation column is operated at absolute pressures in the range from about 2 to about 20 bar.

9. The process according to claim 1, wherein the at least two distillation columns connected in series each include 12 to 50 theoretical plates.

* * * * *